(12) United States Patent
Rowe

(10) Patent No.: US 7,627,151 B2
(45) Date of Patent: *Dec. 1, 2009

(54) SYSTEMS AND METHODS FOR IMPROVED BIOMETRIC FEATURE DEFINITION

(75) Inventor: Robert K. Rowe, Corrales, NM (US)

(73) Assignee: Lumidigm, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/286,156

(22) Filed: Nov. 23, 2005

(65) Prior Publication Data

US 2006/0110015 A1    May 25, 2006

Related U.S. Application Data

(63) Continuation-in-part of application No. 11/115,101, filed on Apr. 25, 2005, which is a continuation-in-part of application No. 11/115,100, filed on Apr. 25, 2005, which is a continuation-in-part of application No. 11/115,075, filed on Apr. 25, 2005, which is a continuation-in-part of application No. 10/818,698, filed on Apr. 5, 2004, now Pat. No. 7,147,153.

(60) Provisional application No. 60/641,991, filed on Jan. 7, 2005, provisional application No. 60/659,024, filed on Mar. 4, 2005, provisional application No. 60/654,354, filed on Feb. 18, 2005, provisional application No. 60/610,802, filed on Sep. 17, 2004, provisional application No. 60/600,867, filed on Aug. 11, 2004, provisional application No. 60/576,364, filed on Jun. 1, 2004, provisional application No. 60/552,662, filed on Mar. 10, 2004, provisional application No. 60/504,594, filed on Sep. 18, 2003, provisional application No. 60/483,281, filed on Jun. 27, 2003, provisional application No. 60/460,247, filed on Apr. 4, 2003.

(51) Int. Cl.
*G06K 9/00* (2006.01)
*G06T 1/00* (2006.01)
*G06T 7/00* (2006.01)

(52) U.S. Cl. .................. 382/124; 382/125; 340/5.53; 340/5.83

(58) Field of Classification Search .............. 382/124, 382/125; 340/5.53, 5.83
See application file for complete search history.

(56) References Cited

U.S. PATENT DOCUMENTS 3,508,830 A    4/1970    Hopkins et al.

(Continued)

FOREIGN PATENT DOCUMENTS

DE    101 53 808    5/2003

(Continued)

OTHER PUBLICATIONS

Lee et al.; "Fingerprint Recognition Using Principal Gabor Basis Function", Proceedings of 2001 International Symposium on Intelligent Multimedia, Video and Speech Processing, May 2-4 2001.*

(Continued)

*Primary Examiner*—John B Strege
(74) *Attorney, Agent, or Firm*—Townsend, Townsend & Crew LLP

(57) ABSTRACT

Methods and systems are provided for performing a biometric function. A purported skin site of an individual is illuminated under distinct optical conditions during a single illumination session for a fixed position of the purported skin site. Light from the purported skin site is received for each of the optical conditions. Images of the purported skin site are generated from the received light. The images are analyzed to identify a biometric feature as a characteristic in a portion of at least one of the images. The biometric function is implemented in accordance with an identification of the biometric feature.

30 Claims, 7 Drawing Sheets

U.S. PATENT DOCUMENTS

| | | | |
|---|---|---|---|
| 3,619,060 A * | 11/1971 | Johnson | 356/71 |
| 3,910,701 A | 10/1975 | Henderson et al. | |
| RE29,008 E | 10/1976 | Ott | |
| 4,035,083 A | 7/1977 | Woodriff et al. | |
| 4,142,797 A | 3/1979 | Astheimer | |
| 4,169,676 A | 10/1979 | Kaiser | |
| 4,170,987 A * | 10/1979 | Anselmo et al. | 600/475 |
| 4,260,220 A | 4/1981 | Whitehead | |
| 4,322,163 A | 3/1982 | Schiller | |
| 4,427,889 A | 1/1984 | Muller | |
| 4,537,484 A | 8/1985 | Fowler | |
| 4,598,715 A | 7/1986 | Machler et al. | |
| 4,653,880 A | 3/1987 | Sting et al. | |
| 4,654,530 A | 3/1987 | Dybwad | |
| 4,655,225 A | 4/1987 | Dahne et al. | |
| 4,656,562 A | 4/1987 | Sugino | |
| 4,657,397 A | 4/1987 | Oehler et al. | |
| 4,661,706 A | 4/1987 | Messerschmidt et al. | |
| 4,684,255 A | 8/1987 | Ford | |
| 4,699,149 A | 10/1987 | Rice | |
| 4,712,912 A | 12/1987 | Messerschmidt | |
| 4,730,882 A | 3/1988 | Messerschmidt | |
| 4,747,147 A | 5/1988 | Sparrow | |
| 4,787,013 A | 11/1988 | Sugino et al. | |
| 4,787,708 A | 11/1988 | Whitehead | |
| 4,830,496 A | 5/1989 | Young | |
| 4,853,542 A | 8/1989 | Milosevic et al. | |
| 4,857,735 A | 8/1989 | Noller | |
| 4,859,064 A | 8/1989 | Messerschmidt et al. | |
| 4,866,644 A | 9/1989 | Shenk et al. | |
| 4,867,557 A | 9/1989 | Takatani et al. | |
| 4,882,492 A | 11/1989 | Schlager | |
| 4,883,953 A | 11/1989 | Koashi et al. | |
| 4,936,680 A | 6/1990 | Henkes et al. | |
| 4,944,021 A | 7/1990 | Hoshino et al. | |
| 4,975,581 A | 12/1990 | Robinson et al. | |
| 5,015,100 A | 5/1991 | Doyle | |
| 5,019,715 A | 5/1991 | Sting et al. | |
| 5,028,787 A | 7/1991 | Rosenthal et al. | |
| 5,051,602 A | 9/1991 | Sting et al. | |
| 5,068,536 A | 11/1991 | Rosenthal | |
| 5,070,874 A | 12/1991 | Barnes et al. | |
| 5,077,803 A | 12/1991 | Kato et al. | |
| 5,109,428 A | 4/1992 | Igaki et al. | |
| 5,146,102 A | 9/1992 | Higuchi et al. | |
| 5,158,082 A | 10/1992 | Jones | |
| 5,163,094 A | 11/1992 | Prokoski et al. | |
| 5,177,802 A * | 1/1993 | Fujimoto et al. | 382/124 |
| 5,178,142 A | 1/1993 | Harjunmaa et al. | |
| 5,179,951 A | 1/1993 | Knudson | |
| 5,204,532 A | 4/1993 | Rosenthal | |
| 5,222,495 A | 6/1993 | Clarke et al. | |
| 5,222,496 A | 6/1993 | Clarke et al. | |
| 5,223,715 A | 6/1993 | Taylor | |
| 5,225,678 A | 7/1993 | Messerschmidt | |
| 5,230,702 A | 7/1993 | Lindsay et al. | |
| 5,237,178 A | 8/1993 | Rosenthal et al. | |
| 5,243,546 A | 9/1993 | Maggard | |
| 5,257,086 A | 10/1993 | Fateley et al. | |
| 5,258,922 A | 11/1993 | Grill | |
| 5,267,152 A | 11/1993 | Yang et al. | |
| 5,268,749 A | 12/1993 | Weber et al. | |
| 5,291,560 A | 3/1994 | Daugman | |
| 5,299,570 A | 4/1994 | Hatschek | |
| 5,303,026 A | 4/1994 | Strobl et al. | |
| 5,311,021 A | 5/1994 | Messerschmidt | |
| 5,313,941 A | 5/1994 | Braig et al. | |
| 5,321,265 A | 6/1994 | Block | |
| 5,331,958 A | 7/1994 | Oppenheimer | |
| 5,348,003 A | 9/1994 | Caro | |
| 5,351,686 A | 10/1994 | Steuer et al. | |
| 5,355,880 A | 10/1994 | Thomas et al. | |
| 5,360,004 A | 11/1994 | Purdy et al. | |
| 5,361,758 A | 11/1994 | Hall et al. | |
| 5,366,903 A | 11/1994 | Lundsgaard et al. | |
| 5,372,135 A | 12/1994 | Mendelson et al. | |
| 5,379,764 A | 1/1995 | Barnes et al. | |
| 5,402,778 A | 4/1995 | Chance | |
| 5,405,315 A | 4/1995 | Khuri et al. | |
| 5,413,098 A * | 5/1995 | Benaron | 600/310 |
| 5,419,321 A | 5/1995 | Evans | |
| 5,435,309 A | 7/1995 | Thomas et al. | |
| 5,441,053 A | 8/1995 | Lodder et al. | |
| 5,452,723 A | 9/1995 | Wu et al. | |
| 5,459,317 A | 10/1995 | Small et al. | |
| 5,459,677 A | 10/1995 | Kowalski et al. | |
| 5,460,177 A | 10/1995 | Purdy et al. | |
| 5,483,335 A | 1/1996 | Tobias | |
| 5,494,032 A | 2/1996 | Robinson et al. | |
| 5,505,726 A | 4/1996 | Meserol | |
| 5,507,723 A | 4/1996 | Keshaviah | |
| 5,515,847 A | 5/1996 | Braig et al. | |
| 5,518,623 A | 5/1996 | Keshaviah et al. | |
| 5,523,054 A | 6/1996 | Switalski et al. | |
| 5,533,509 A | 7/1996 | Koashi et al. | |
| 5,537,208 A | 7/1996 | Bertram et al. | |
| 5,539,207 A | 7/1996 | Wong et al. | |
| 5,552,997 A | 9/1996 | Massart | |
| 5,559,504 A | 9/1996 | Itsumi et al. | |
| 5,568,251 A | 10/1996 | Davies et al. | |
| 5,596,992 A | 1/1997 | Haaland et al. | |
| 5,606,164 A | 2/1997 | Price et al. | |
| 5,613,014 A * | 3/1997 | Eshera et al. | 382/124 |
| 5,630,413 A | 5/1997 | Thomas et al. | |
| 5,636,633 A | 6/1997 | Messerschmidt et al. | |
| 5,655,530 A | 8/1997 | Messerschmidt | |
| 5,672,864 A | 9/1997 | Kaplan | |
| 5,672,875 A | 9/1997 | Block et al. | |
| 5,677,762 A | 10/1997 | Ortyn et al. | |
| 5,681,273 A | 10/1997 | Brown | |
| 5,708,593 A | 1/1998 | Saby et al. | |
| 5,719,399 A | 2/1998 | Alfano et al. | |
| 5,719,950 A | 2/1998 | Osten et al. | |
| 5,724,268 A | 3/1998 | Sodickson et al. | |
| 5,737,439 A | 4/1998 | Lapsley et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,751,835 A | 5/1998 | Topping et al. | |
| 5,761,330 A | 6/1998 | Stoianov et al. | |
| 5,782,755 A | 7/1998 | Chance et al. | |
| 5,792,050 A | 8/1998 | Alam et al. | |
| 5,792,053 A | 8/1998 | Skladner et al. | |
| 5,793,881 A | 8/1998 | Stiver et al. | |
| 5,796,858 A | 8/1998 | Zhou et al. | |
| 5,808,739 A | 9/1998 | Turner et al. | |
| 5,818,048 A | 10/1998 | Sodickson et al. | |
| 5,823,951 A | 10/1998 | Messerschmidt | |
| 5,828,066 A | 10/1998 | Messerschmidt | |
| 5,830,132 A | 11/1998 | Robinson | |
| 5,830,133 A | 11/1998 | Osten et al. | |
| 5,850,623 A | 12/1998 | Carman, Jr. et al. | |
| 5,853,370 A | 12/1998 | Chance et al. | |
| 5,857,462 A | 1/1999 | Thomas et al. | |
| 5,859,420 A * | 1/1999 | Borza | 250/208.1 |
| 5,860,421 A | 1/1999 | Eppstein et al. | |
| 5,867,265 A | 2/1999 | Thomas | |
| 5,886,347 A | 3/1999 | Inoue et al. | |
| 5,902,033 A | 5/1999 | Levis et al. | |
| 5,914,780 A | 6/1999 | Turner et al. | |
| 5,929,443 A | 7/1999 | Alfano et al. | |
| 5,933,792 A | 8/1999 | Anderson et al. | |
| 5,935,062 A | 8/1999 | Messerschmidt et al. | |
| 5,945,676 A | 8/1999 | Khalil et al. | |

| | | | | | | |
|---|---|---|---|---|---|---|
| 5,949,543 A | 9/1999 | Bleier et al. | 6,419,361 B2 * | 7/2002 | Cabib et al. | 351/221 |
| 5,957,841 A | 9/1999 | Maruo et al. | 6,483,929 B1 | 11/2002 | Murakami et al. | |
| 5,961,449 A | 10/1999 | Toida et al. | 6,504,614 B1 | 1/2003 | Messerschmidt et al. | |
| 5,963,319 A | 10/1999 | Jarvis et al. | 6,537,225 B1 | 3/2003 | Mills | |
| 5,987,346 A | 11/1999 | Benaron et al. | 6,560,352 B2 | 5/2003 | Rowe et al. | |
| 5,999,637 A | 12/1999 | Toyoda et al. | 6,574,490 B2 | 6/2003 | Abbink et al. | |
| 6,005,722 A | 12/1999 | Butterworth et al. | 6,597,945 B2 * | 7/2003 | Marksteiner | 600/547 |
| 6,016,435 A | 1/2000 | Maruo et al. | 6,606,509 B2 | 8/2003 | Schmitt | |
| 6,025,597 A | 2/2000 | Sterling et al. | 6,628,809 B1 | 9/2003 | Rowe et al. | |
| 6,026,314 A | 2/2000 | Amerov et al. | 6,631,199 B1 | 10/2003 | Topping et al. | |
| 6,028,773 A | 2/2000 | Hundt | 6,741,729 B2 | 5/2004 | Bjorn et al. | |
| 6,031,609 A | 2/2000 | Funk et al. | 6,799,275 B1 | 9/2004 | Bjorn | |
| 6,034,370 A | 3/2000 | Messerschmidt | 6,799,726 B2 | 10/2004 | Stockhammer | |
| 6,040,578 A | 3/2000 | Malin et al. | 6,816,605 B2 | 11/2004 | Rowe et al. | |
| 6,041,247 A | 3/2000 | Weckstrom et al. | 6,825,930 B2 | 11/2004 | Cronin et al. | |
| 6,041,410 A | 3/2000 | Hsu et al. | 6,928,181 B2 | 8/2005 | Brooks | |
| 6,043,492 A | 3/2000 | Lee et al. | 6,937,885 B1 * | 8/2005 | Lewis et al. | 600/476 |
| 6,044,285 A | 3/2000 | Chaiken et al. | 6,958,194 B1 | 10/2005 | Hopper et al. | |
| 6,045,502 A | 4/2000 | Eppstein et al. | 6,995,384 B2 | 2/2006 | Lee et al. | |
| 6,046,808 A | 4/2000 | Fateley | 7,147,153 B2 * | 12/2006 | Rowe et al. | 235/382 |
| 6,049,727 A | 4/2000 | Crothall | 2002/0009213 A1 | 1/2002 | Rowe et al. | |
| 6,056,738 A | 5/2000 | Marchitto et al. | 2002/0101566 A1 * | 8/2002 | Elsner et al. | 351/200 |
| 6,057,925 A | 5/2000 | Anthon | 2002/0171834 A1 | 11/2002 | Rowe et al. | |
| 6,061,581 A | 5/2000 | Alam et al. | 2002/0183624 A1 * | 12/2002 | Rowe et al. | 600/476 |
| 6,061,582 A | 5/2000 | Small et al. | 2003/0044051 A1 | 3/2003 | Fujieda | |
| 6,066,847 A | 5/2000 | Rosenthal | 2003/0078504 A1 | 4/2003 | Rowe | |
| 6,069,689 A | 5/2000 | Zeng et al. | 2003/0223621 A1 | 12/2003 | Rowe et al. | |
| 6,070,093 A | 5/2000 | Oosta et al. | 2004/0008875 A1 | 1/2004 | Linares | |
| 6,073,037 A | 6/2000 | Alam et al. | 2004/0047493 A1 | 3/2004 | Rowe et al. | |
| 6,088,605 A | 7/2000 | Griffith et al. | 2004/0114783 A1 | 6/2004 | Spycher et al. | |
| 6,088,607 A | 7/2000 | Diab et al. | 2004/0179722 A1 | 9/2004 | Moritoki et al. | |
| 6,097,035 A | 8/2000 | Belongie et al. | 2004/0240712 A1 | 12/2004 | Rowe et al. | |
| 6,100,811 A | 8/2000 | Hsu et al. | 2005/0007582 A1 | 1/2005 | Villers et al. | |
| 6,115,484 A | 9/2000 | Bowker et al. | 2005/0180620 A1 * | 8/2005 | Takiguchi | 382/128 |
| 6,115,673 A | 9/2000 | Malin et al. | 2005/0185847 A1 | 8/2005 | Rowe | |
| 6,122,042 A | 9/2000 | Wunderman et al. | 2005/0205667 A1 | 9/2005 | Rowe | |
| 6,122,394 A | 9/2000 | Neukermans et al. | 2005/0265585 A1 | 12/2005 | Rowe | |
| 6,122,737 A | 9/2000 | Bjorn et al. | 2005/0265586 A1 | 12/2005 | Rowe et al. | |
| 6,125,192 A | 9/2000 | Bjorn et al. | 2005/0271258 A1 | 12/2005 | Rowe | |
| 6,141,101 A | 10/2000 | Bleier et al. | 2006/0002597 A1 | 1/2006 | Rowe | |
| 6,147,749 A | 11/2000 | Kubo et al. | 2006/0002598 A1 | 1/2006 | Rowe et al. | |
| 6,148,094 A | 11/2000 | Kinsella | 2006/0115128 A1 * | 6/2006 | Mainguet | 382/115 |
| 6,152,876 A | 11/2000 | Robinson et al. | 2006/0202028 A1 | 9/2006 | Rowe | |
| 6,154,658 A | 11/2000 | Caci | 2006/0210120 A1 | 9/2006 | Rowe | |
| 6,157,041 A | 12/2000 | Thomas et al. | 2006/0274921 A1 | 12/2006 | Rowe | |
| 6,159,147 A | 12/2000 | Lichter et al. | | | | |
| 6,172,743 B1 | 1/2001 | Kley et al. | | FOREIGN PATENT DOCUMENTS | | |
| 6,175,407 B1 | 1/2001 | Sartor | | | | |
| 6,181,414 B1 | 1/2001 | Raz et al. | EP | 0 280 418 A1 | 8/1988 | |
| 6,181,958 B1 | 1/2001 | Steuer et al. | EP | 0 372 748 | 6/1990 | |
| 6,188,781 B1 * | 2/2001 | Brownlee 382/127 | EP | 0 897 164 A2 | 2/1999 | |
| 6,208,749 B1 | 3/2001 | Gutkowicz-Krusin | EP | 0 924 656 A2 | 6/1999 | |
| 6,212,424 B1 | 4/2001 | Robinson | EP | 1 353 292 | 10/2003 | |
| 6,226,541 B1 | 5/2001 | Eppstein et al. | EP | 1 434 162 A2 | 6/2004 | |
| 6,230,034 B1 | 5/2001 | Messerschmidt et al. | FR | 2761180 A1 * | 9/1998 | |
| 6,240,306 B1 | 5/2001 | Rohrscheib et al. | JP | 2001-184490 A | 7/2001 | |
| 6,240,309 B1 | 5/2001 | Yamashita et al. | JP | 2002-133402 A | 5/2002 | |
| 6,241,663 B1 | 6/2001 | Wu et al. | JP | 2003-308520 A | 10/2003 | |
| 6,256,523 B1 | 7/2001 | Diab et al. | WO | WO 92/00513 A1 | 1/1992 | |
| 6,272,367 B1 | 8/2001 | Chance | WO | WO 92/17765 A1 | 10/1992 | |
| 6,280,381 B1 | 8/2001 | Malin et al. | WO | WO 93/07801 A1 | 4/1993 | |
| 6,282,303 B1 | 8/2001 | Brownlee | WO | WO 01/18332 A1 | 3/2001 | |
| 6,285,895 B1 | 9/2001 | Ristolainen et al. | WO | WO 01/27882 A2 | 4/2001 | |
| 6,292,576 B1 * | 9/2001 | Brownlee 382/124 | WO | WO 01/52180 A1 | 7/2001 | |
| 6,301,375 B1 | 10/2001 | Choi | WO | WO 01/52726 A1 | 7/2001 | |
| 6,301,815 B1 | 10/2001 | Sliwa | WO | WO 01/53805 A1 | 7/2001 | |
| 6,304,767 B1 | 10/2001 | Soller et al. | WO | WO 02/084605 A2 | 10/2002 | |
| 6,307,633 B1 | 10/2001 | Mandella et al. | WO | WO 02/099393 A2 | 12/2002 | |
| 6,309,884 B1 | 10/2001 | Cooper et al. | WO | WO 03/096272 A1 | 11/2003 | |
| 6,317,507 B1 | 11/2001 | Dolfing et al. | WO | WO 03096272 * | 11/2003 | |
| 6,324,310 B1 | 11/2001 | Brownlee | WO | WO 03096272 A1 * | 11/2003 | |
| 6,330,346 B1 | 12/2001 | Peterson et al. | WO | 2004-068394 | 8/2004 | |
| 6,404,904 B1 * | 6/2002 | Einighammer et al. 382/124 | | | | |

| | | | |
|---|---|---|---|
| WO | WO 2004/068388 A2 | 8/2004 | |
| WO | WO 2004/068394 A1 | 8/2004 | |
| WO | WO 2004068394 A1 * | 8/2004 | |
| WO | WO 2004/090786 | 10/2004 | |

OTHER PUBLICATIONS

Selvaraj et al, Fingerprint Verification Using Wavelet Transform, Proceedings of the fifth international conference on computational intelligence and multimedia applications, IEEE, 2003.*

Pan et al.; "Face Recognition in Hyperspectral Images", IEEE Transactions on Pattern Analysis and Machine Intelligence, vol. 25, No. 12, Dec. 2003.*

Bantle, John P. et al., "Glucose Measurement in Patients With Diabetes Mellitus With Dermal Interstitial Fluid," Mosby-Year Book, Inc., 9 pages, 1997.

Berkoben, Michael S. et al., "Vascular Access For Hemodialysis," Clinical Dialysis, Third Edition, pp. 2 cover pages and 26-45, 1995.

Bleyer, Anthony J. et al., "The Costs Of Hospitalizations Due To Hemodialysis Access Management," Nephrology News & Issues, pp. 19, 20 and 22, Jan. 1995.

Daugirdas, JT et al., "Comparison Of Methods To Predict The Equilibrated Kt/V (eKt/V) In The Hemo Study," National Institutes of Health, pp. 1-28, Aug. 20, 1996.

Demos, S. G. et al., "Optical Fingerprinting Using Polarisation Contrast Improvement," Electronics Letters, vol. 33, No. 7, pp. 582-584, Mar. 27, 1997.

Depner, Thomas A. et al., "Clinical Measurement Of Blood Flow In Hemodialysis Access Fistulae And Grafts By Ultrasound Dilution," Division of Nephrology, University of California, pp. M745-M748, published on or before Oct. 30, 1997.

Fresenius USA, "Determination Of Delivered Therapy Through Measurement Of Effective Clearance," 2 pages, Dec. 1994.

Hakim, Raymond M. et al., "Effects Of Dose Of Dialysis On Morbidity And Mortality," American Journal of Kidney Diseases, vol. 23, No. 5, pp. 661-669, May 1994.

Jacobs, Paul et al., "A Disposable Urea Sensor For Continuous Monitoring Of Hemodialysis Efficiency," ASAIO Journal, pp. M353-M358, 1993.

Keshaviah, Prakash R. et al., "On-Line Monitoring Of The Delivery Of The Hemodialysis Prescription," Pediatric Nephrology, vol. 9, pp. S2-S8, 1995.

Krivitski, Nikolai M., "Theory And Validation Of Access Flow Measurement By Dilution Technique During Hemodialysis," Kidney International, vol. 48, pp. 244-250, 1995.

Marbach, Ralf, "Measurement Techniques For IR Spectroscopic Blood Glucose Determination," Fortschritt Bericht, Series 8: Measurement And Control Technology, No. 346, pp. cover and 1-158. Mar. 28, 1994.

Mardia, K.V. et al., "Chapter 11—Discriminant Analysis," Multivariate Analysis, pp. 2 cover pages and 300-325, 1979.

Nichols, Michael G. et al., "Design And Testing Of A White-Light, Steady-State Diffuse Reflectance Spectrometer For Determination Of Optical Properties Of Highly Scattering Systems," Applied Optics, vol. 36, No. 1, pp. 93-104, Jan. 1, 1997.

Ripley, B. D., "Chapter 3—Linear Discriminant Analysis," Pattern Recognition And Neural Networks, pp. 3 cover pages and 91-120, 1996.

Ronco, C. et al., "On-Line Urea Monitoring : A Further Step Towards Adequate Dialysis Prescription And Delivery," The International Journal Of Artificial Organs, vol. 18, No. 9, pp. 534-543, 1995.

Service, F. John et al., "Dermal Interstitial Glucose As An Indicator Of Ambient Glycemia," Diabetes Care, vol. 20, No. 9, 8 pages, Aug. 1997.

Sherman, Richard A., "Chapter 4—Recirculation In The Hemodialysis Access," Principles and Practice of Dialysis, pp. 2 cover pages and 38-46, 1994.

Sherman, Richard A., "The Measurement Of Dialysis Access Recirculation," American Journal of Kidney Diseases, vol. 22, No. 4, pp. 616-621, Oct. 1993.

Steuer, Robert R. et al., "A New Optical Technique For Monitoring Hematocrit And Circulating Blood Volume: Its Application in Renal Dialysis," Dialysis & Transplantation, vol. 22, No. 5, pp. 260-265, May 1993.

Webb, Paul, "Temperatures Of Skin, Subcutaneous Tissue, Muscle And Core In Resting Men In Cold, Comfortable And Hot Conditions," European Journal of Applied Physiology, vol. 64, pp. 471-476, 1992.

Zavala, Albert et al., "Using Fingerprint Measures To Predict Other Anthropometric Variables," Human Factors, vol. 17, No. 6, pp. 591-602, 1975.

Nixon, Kristin A., et al., "Novel Spectroscopy-Based Technology for Biometric and Liveness Verification", Biometric Technology for Human Identification, Proceedings of SPIE, vol. 5404, No. 1, XP-002458441, Apr. 12-13, 2004, pp. 287-295 (ISSN: 0277-786X).

Anderson, C. E. et al., "Fundamentals of Calibration Transfer Through Procrustes Analysis," Appln. Spectros., vol. 53, No. 10 (1999) p. 1268-1276.

Ashboum, Julian, Biometrics; Advanced Identity Verification, Springer, 2000, pp. 63-64).

Blank, T.B. et al., "Transfer of Near-Infrared Multivariate Calibrations Without Standards," Anal. Chem., vol. 68 (1996) p. 2987.

Brasunas John C. et al., "Uniform Time-Sampling Fourier Transform Spectroscopy," Applied Optics, vol. 36, No. 10, Apr. 11, 1997, pp. 2206-22 10.

Brault, James W., "New Approach to High-Precision Fourier Transform spectrometer Design," Applied Optics, Vo. 35, No. 16, Jun. 1, 1996, pp. 2891-2896.

Brochure entitled "Improve the Clinical Outcome of Every Patient", In Line Diagnostics, published on or before Oct. 30, 1997, 2 pages.

Cassarly, W.J. et al., "Distributed Lighting Systems: Uniform Light Delivery," Source Unknown, pp. 1698-1702.

Chang, Chong-Min et al., "An Uniform Rectangular Illuminating Optical System for Liquid Crystal Light Valve Projectors," Euro Display '96 (1996) pp. 257-260.

Coyne, Lawrence J. et al., "Distributive Fiber Optic couplers Using Rectangular Lightguides as Mixing Elements," (Information Gatekeepers, Inc. Brookline, MA, 1979) pp. 160-164.

de Noord, Onno E., "Multivariate Calibration Standardization," Chemometrics and intelligent Laboratory Systems 25, (1994) pp. 85-97.

Despain, Alvin M. et al., "A Large-Aperture Field-Widened Interferometer-Spectrometer for Airglow Studies," Aspen International Conference on Fourier Spectroscopy, 1970, pp. 293-300.

Faber, Nicolaas, "Multivariate Sensitivity for the Interpretation of the Effect of Spectral Pretreatment Methods on Near-Infrared Calibration Model Predictions," Analytical Chemistry, vol. 71, No. 3, Feb. 1, 1999, pp. 557-565.

Geladi, Paul et al., A Multivariate NIR Study of Skin Alterations in Diabetic Patients as Compared to Control Subj ects,' J. Near Infrared Spectrosc., vol. 8 (2000) pp. 217-227.

Pan et al., "Face Recognition in Hyperspectral Images", IEEE Transactions on Pattern Analysis and Machine Intelligence vol. 25, No. 12, Dec. 2003.

Ross et al., "A hybrid fingerprint matcher", Pattern Recognition 36, The Journal of the Pattern Recognition Society, 2003 Elsevier Science Ltd., pp. 1661-1673.

U.S. Appl. No. 11/115,075, Office Action, 26 pages, Nov. 13, 2006.
U.S. Appl. No. 11/115,075, Office Action, 9 pages, May 1, 2007.
U.S. Appl. No. 11/115,075, Office Action, 7 pages, Aug. 31, 2007.
U.S. Appl. No. 11/115,075, Office Action, 9 pages, Feb. 1, 2008.
U.S. Appl. No. 11/115,075, Advisory Action, 3 pages, Apr. 24, 2008.
U.S. Appl. No. 11/115,100, Office Action, 30 pages, Nov. 14, 2006.
U.S. Appl. No. 11/115,100, Office Action, 10 pages, May 1, 2007.
U.S. Appl. No. 11/115,100, Office Action, 9 pages, Aug. 9, 2007.
U.S. Appl. No. 11/115,101, Office Action, 24 pages, Dec. 13, 2006.
U.S. Appl. No. 11/115,101, Office Action, 17 pages, May 9, 2007.

* cited by examiner

SYSTEMS AND METHODS FOR IMPROVED BIOMETRIC FEATURE DEFINITION

CROSS-REFERENCES TO RELATED APPLICATIONS

This application is a nonprovisional of, and claims the benefit of the filing date of, U.S. Prov. Pat. Appl. No. 60/641,991, entitled "SYSTEMS AND METHODS FOR IMPROVED BIOMETRIC FEATURE DEFINITION," filed Jan. 7, 2005, by Robert K. Rowe.

This application is a continuation-in-part of U.S. patent application Ser. No. 10/818,698, entitled "MULTISPECTRAL BIOMETRIC SENSOR," filed Apr. 5, 2004, by Robert K. Row. et al., which is a nonprovisional of each of U.S. Prov. Pat. Appl. No. 60/460,247, filed Apr. 4, 2003, U.S. Prov. Pat. Appl. No. 60/483,281, filed Jun. 27, 2003, U.S. Prov. Pat. Appl. No. 60/504,594, filed Sep. 18, 2003, and U.S. Prov. Pat. Appl. No. 60/552,662, filed Mar. 10, 2004.

This application is also a continuation-in-part of U.S. patent application Ser. No. 11/115,100, entitled "MULTISPECTRAL IMAGING BIOMETRICS," filed Apr. 25, 2005, by Robert K. Rowe, which is a nonprovisional of each of U.S. Prov. Pat. Appl. No. 60/576,364, filed Jun. 1, 2004, U.S. Prov. Pat. Appl. No. 60/600,867, filed Aug. 11, 2004, U.S. Prov. Pat. Appl. No. 60/610,802, filed Sep. 17, 2004, U.S. Prov. Pat. Appl. No. 60/654,354, filed Feb. 18, 2005, and U.S. Prov. Pat. Appl. No. 60/659,024, filed Mar. 4, 2005.

This application is also a continuation-in-part of U.S. patent application Ser. No. 11/115,101, entitled "MULTISPECTRAL BIOMETRIC IMAGING," filed Apr. 25, 2005, by Robert K. Rowe and Stephen P. Corcoran, which is a nonprovisional of each of U.S. Prov. Pat. Appl. No. 60/576,364, filed Jun. 1, 2004, U.S. Prov. Pat. Appl. No. 60/600,867, filed Aug. 11, 2004, U.S. Prov. Pat. Appl. No. 60/610,802, filed Sep. 17, 2004, U.S. Prov. Pat. Appl. No. 60/654,354, filed Feb. 18, 2005, and U.S. Prov. Pat. Appl. No. 60/659,024, filed Mar. 4, 2005.

This application is also a continuation-in-part of U.S. patent application Ser. No. 11/115,075, entitled "MULTISPECTRAL LIVENESS DETERMINATION," FILED Apr. 25, 2005, by Robert K. Rowe, which is a nonprovisional of each of U.S. Prov. Pat. Appl. No. 60/576,364, filed Jun. 1, 2004, U.S. Prov. Pat. Appl. No. 60/600,867, filed Aug. 11, 2004, U.S. Prov. Pat. Appl. No. 60/610,802, filed Sep. 17, 2004, U.S. Prov. Pat. Appl. No. 60/654,354, filed Feb. 18, 2005, and U.S. Prov. Pat. Appl. No. 60/659,024, filed Mar. 4, 2005.

This application is related to the following copending, commonly assigned applications: U.S. Prov. Pat. Appl. No. 60/610,802, entitled "FINGERPRINT SPOOF DETECTION USING MULTISPECTRAL IMAGING," filed Sep. 17, 2004, by Robert K. Rowe; and U.S. patent application Ser. No. 11/015,732, entitled "COMBINED TOTAL-INTERNAL-REFLECTANCE AND TISSUE IMAGING SYSTEMS AND METHODS," filed Dec. 17, 2004, by Robert K. Rowe.

Each application identified in the paragraphs above is incorporated herein by reference in its entirety for all purposes. Such incorporation by reference specifically includes the Appendices of U.S. Prov. Pat. Appl. No. 60/641,991.

BACKGROUND OF THE INVENTION

This application relates generally to biometrics. More specifically, this application relates to systems and methods for improved biometric feature definition.

Achieving adequate performance from a biometric system relies fundamentally on the ability to isolate biometric features within a dataset from other portions of the dataset—the biometric features may then be used to identify a person, while the other portions of the dataset are generally unrelated to a person's identity. Consider, for example, the case of a fingerprint sensor. Each time a fingerprint image is collected, it is affected by a variety of phenomena that make the image unique. This is true even when the same fingerprint is being imaged. For example, each finger placement on the sensor results in a different portion of the finger coming into contact with the sensor and being imaged. Differences in orientation and pressure of the finger cause distortions of the skin, changes in image contrast, and other artifacts that affect the characteristics of the fingerprint image. The sensor itself may also introduce artifacts into the image that vary from image to image. These sensor artifacts may include fixed-pattern noise that varies in some manner across the image plane and a variety of high-frequency image noise sources, including shot noise and dark noise among other types of noise sources.

Because of the presence of these kinds of nonbiometric sources of variation, two fingerprint images cannot generally be compared directly by a simple operation such as an image subtraction to determine whether they originate from the same person. Instead, salient features of the image are identified, both in the images used to populate an enrollment database and in test images. These features are then compared to determine whether a sufficient number are present and in approximately the same relative spatial location in the two images. If so, the images are said to match; if not, the images are determined not to match.

Many existing fingerprint sensors require direct contact between the finger and the sensor to collect an image. In cases where the finger is not making adequate contact with the sensor, the area of direct contact between the finger and the sensor is reduced, resulting in the collection of less biometric information. Generally, fewer biometric features can be extracted from this reduced image area, resulting in a degraded ability to properly determine matching fingerprint images.

To address some of these deficiencies with properly defining fingerprint features, many systems require that the user take more than one sample for enrollment in the system database. In this way, multiple images may be acquired of the same finger and analyzed to detect features that are common across each enrollment image. But the ability to determine the presence of a true biometric feature is still compromised by the differences in finger orientation, translation, rotation, distortion, and other image artifacts across the set of enrollment images. In addition, the ability to collect and compare multiple fingerprint images is usually only viable during the enrollment procedure. During the normal execution of biometric functions such as identification or verification, most applications require that the biometric sensor operate using a single, rapidly acquired fingerprint image. In such scenarios, there is no opportunity to enhance the feature detection of a test sample by using multiple images.

Fingerprint sensors also typically collect images that originate with the external characteristics of the skin of a finger. But these external characteristics are subject to wear, contamination, or changes that result from differences in environmental conditions, all of which may further compromise the definition of fingerprint features. Furthermore, the surface characteristics are relatively easy to replicate based upon a latent print of the fingerprint left on a smooth, nonporous surface. Thus, the reliance of conventional fingerprint sensors on measuring only the surface characteristics of the finger has a number of negative consequences. First, the number and quality of biometric features that may be detected is limited to those features present on the surface skin, which may be worn or missing. Second, a sensor that relies exclusively on features present on the external surface skin is susceptible to a security breach using an artificial replica of an authorized fingerprint pattern.

Because the finger is an approximately cylindrical object, there is a tendency for the skin to pull away from the sensor surface towards the edges of the imaging region. For this reason, fingerprint images collected for law-enforcement applications are typically collected using a "rolled" procedure. In such a procedure, the image of the finger is acquired as the finger is rolled along the sensor surface so that more portions of the finger come into contact with the sensor to permit them to be imaged. This procedure is time consuming, awkward for the user, and generally requires a skilled operator to assist the proper collection of such data. Consequently, this method of fingerprint image collection is not generally used by automated and unattended biometric sensors, even though the greater image area could in principle provide improved performance.

There is accordingly a general need in the art for improved methods and systems for collecting biometric measurements form which biometric features may be defined.

BRIEF SUMMARY OF THE INVENTION

Embodiments of the invention provide methods for performing a biometric function. A purported skin site of an individual is illuminated under a plurality of distinct optical conditions during a single illumination session for a substantially fixed position of the purported skin site. Light from the purported skin site is received for each of the plurality of distinct optical conditions. A plurality of images of the purported skin site are generated from the received light. The plurality of images are analyzed to identify a biometric feature as a characteristic in a portion of at least one of the images. The biometric function is implemented in accordance with an identification of the biometric feature.

In some embodiments, the biometric feature is a characteristic common to respective portions of multiple of the plurality of images. The biometric feature may also comprise a plurality of biometric features in some embodiments. In such instances, the plurality of images may be analyzed by identifying a spatial relationship among the plurality of images from a condition that placement of the purported skin site is common for each of the plurality of images, permitting the plurality of biometric features to be identified from the identified spatial relationship. Implementation of the biometric function in such embodiments may also comprise comparing the plurality of biometric features with a set of biometric features stored in a database relating sets of biometric features with identified individuals.

The purported skin site may comprise a finger of the individual in one embodiment, with the plurality of images comprising a fingerprint image and the biometric feature comprising a minutia point of the fingerprint image. In other embodiments, the biometric feature comprises a representation of ridges and valleys on the skin site. In still other embodiments, the biometric feature comprises a characteristic of a presence of blood vessels beneath a surface of the purported skin site. Examples of the plurality of distinct optical conditions include distinct illumination wavelengths, distinct polarization conditions, distinct illumination or imaging orientations, different focal planes, and the like. Examples of implementation of the biometric function include identifying the individual or verifying an identity of the individual. In some embodiments, light received from the purported skin site may comprise light scattered from beneath a surface of the purported skin site. The plurality of images may comprise a total-internal-reflectance ("TIR") image of the skin site and a non-TIR image of the skin site.

In one embodiment, the purported skin site comprises a finger of the individual and is in contact with a platen. The plurality of images comprises a fingerprint image, and the biometric feature comprises a biometric feature of the individual identified outside an area of contact of the purported skin site with the platen.

The plurality of images may be analyzed in some instances by skeletonizing the at least one of the images, permitting the biometric feature to be identified in the skeletonized at least one of the images. In another embodiment, the plurality of images is analyzed by performing a decomposition of the portion of the at least one of the images onto a set of basis functions, with the biometric feature comprising a set of coefficients formed by the decomposition.

The methods of performing a biometric function may be embodied in a biometric system. The biometric system comprises a platen, an illumination source, an imaging system, and a controller. The platen is adapted for placement of a purported skin site by an individual. The illumination source is disposed to illuminate the purported skin site when placed on the platen. The imaging system is disposed to receive light from the purported skin site. The controller includes instructions for implementing the methods as described above with the biometric system.

BRIEF DESCRIPTION OF THE DRAWINGS

A further understanding of the nature and advantages of the present invention may be realized by reference to the remaining portions of the specification and the drawings wherein like reference labels are used through the several drawings to refer to similar components. In some instances, reference labels include a numerical portion followed by a latin-letter suffix; reference to only the numerical portion of reference labels is intended to refer collectively to all reference labels that have that numerical portion but different latin- letter suffices.

DETAILED DESCRIPTION OF THE INVENTION

Figure 1:
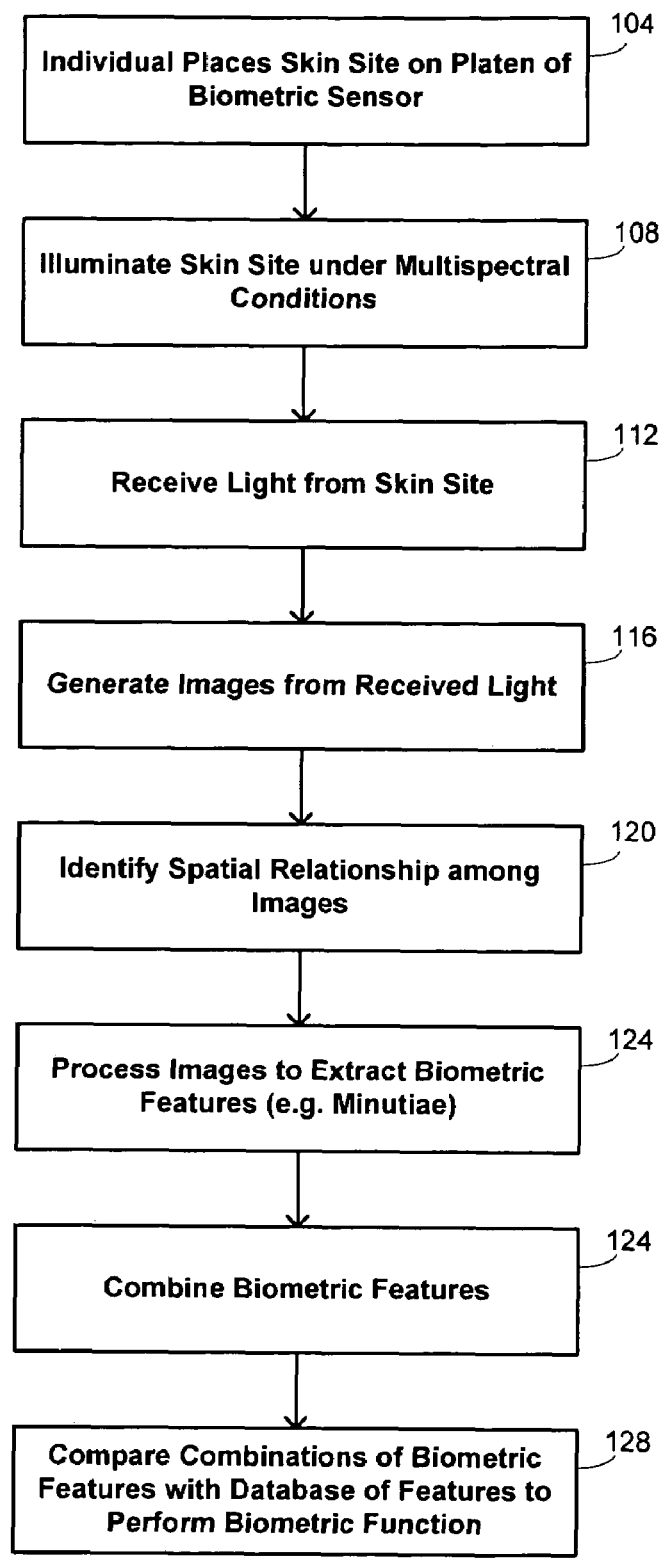
FIG. 1 is a flow diagram that summarizes aspects of several embodiments of the invention.

Embodiments of the invention provide systems and methods for performing a biometric function that make use of the acquisition of multiple images of a skin site taken under different optical conditions during a single illumination session. The images thus contain different information about the skin site that may be combined in various manners to produce reliable definitions of biometric features. Use of a single illumination session permits the images to be generated for a substantially fixed position of the skin site, removing uncertainties in the relative orientation of features between images and resulting in increased accuracy and reduced processing requirements.

The term "biometrics" refers generally to the statistical analysis of characteristics of living bodies. One category of biometrics includes "biometric identification," which commonly operates under one of two modes to provide automatic identification of people or to verify purported identities of people. As used herein, reference to "biometric features," or sometimes to just "features," is intended to refer to those portions of an image or a set of images that contain information relevant to biometric tasks such as biometric identification, identity verification, determination of sample authenticity, liveness, and the like. The term "portion" is intended to refer to a part of an object that excludes the whole of the object; thus, a "portion" of an image refers to a part of the image that is not the entire image. In different specific embodiments, a portion of an image may thus refer to a part of an image that has an area less than 10% of the area of the image, less than 5% of the area of the image, less than 2% of the area of the image, less than 1% of the area of the image, less than 0.5% of the area of the image, less than 0.2% of the area of the image, less than 0.1% of the area of the image, or a different fraction of the area of the image.

In cases where the skin sites comprise fingers, biometric features thus include "minutia points," which are well known in the fingerprint arts to be local fingerprint ridge characteristics that occur either at a ridge bifurcation or at a ridge ending. In other instances where the skin sites comprise fingers, the biometric features may be particular patterns formed in a portion of the fingerprint image by ridges and valleys of the fingerprint.

Skin sites applicable to the measurements described herein include all surfaces and all joints of the fingers and thumbs, the fingernails and nail beds, the palms, the backs of the hands, the wrists and forearms, the face, the eyes, the ears, and all other external surfaces of the body. While the discussion below sometimes makes specific reference to "fingers" in providing examples of specific embodiments, it should be understood that these embodiments are merely exemplary and that other embodiments may use skin sites at other body parts.

The set of all images collected under a plurality of distinct optical conditions during a single illumination session is referred to herein as "multispectral data". The different optical conditions may include differences in polarization conditions, differences in illumination angle, differences in imaging angle, differences in illumination wavelength, and differences in the position of the plane of the skin site being imaged, referred herein as the "focal plane." In some optical conditions the resulting images are significantly affected by the presence and distribution of total-internal-reflectance ("TIR") phenomena at the interface between the sample and the platen. These images are referred to herein as "TIR images." In some optical conditions, the resulting images are substantially unaffected by the presence or absence of TIR effects at the platen. These images are referred to herein as "direct images."

Merely by way of example, embodiments in which the multispectral data include images acquired with different illumination wavelengths may have wavelengths from near-ultraviolet (UV-A, 320-400 nm) to mid-infrared (~5 µm). Silicon-based imaging arrays may be used in such embodiments with a range of detectable wavelengths that vary from about 300 nm to about 1100 nm. In these cases, the illumination wavelengths may advantageously be chosen to lie within the detectable range. In some cases, the illumination wavelengths are within the visible spectral region (400-700 nm). As used herein, reference to "discrete wavelengths" is intended to refer to sets of wavelengths or wavelength bands that are treated as single binned units—for each binned unit, information is extracted only from the binned unit as a whole, and not from individual wavelength subsets of the binned unit. In some cases, the binned units may be discontinuous so that when a plurality of discrete wavelengths are provided, some wavelength between any pair of the wavelengths or wavelength bands is not provided, but this is not required.

Embodiments in which the multispectral data include images acquired under different polarization conditions may include images acquired with crossed polarization states, with parallel polarization states, and/or with no polarization. Polarization of the light may be linear or elliptical. In the case of linear polarization, "crossed" means that the optical axes of the polarizers are substantially orthogonal. In the case of elliptical polarization, "crossed" means that the polarizers are of substantially the opposite sense (right-circular versus left-circular).

Embodiments in which the multispectral data include images acquired with different illumination angles may be achieved by providing the illumination light at different angles relative to a platen on which the skin site is placed. In some cases, the images are formed from illumination light that is substantially at an angle less than the critical angle formed by the skin-platen interface. In other cases, the images are formed from illumination light that is substantially at an angle greater than the critical angle formed by the skin-platen interface.

Embodiments in which the multispectral data include images acquired with different imaging angles may be achieved with detector arrays that are oriented at different angles to a platen on which the skin site is placed. In some cases, some of the images are formed from a detector array that views the skin site at an angle less than the critical angle formed by the skin-platen interface. In other cases, some of the images are formed from a detector array that views the skin site at an angle greater than the critical angle formed by the skin-platen interface.

Embodiments in which the multispectral data include images acquired at different focal planes may be achieved with an imaging system that has variable focal settings to properly image regions of the sample that are not in direct contact with the platen. For instance, in a first such image, the focus of the imaging system may be set to image the interface between the skin site and the platen. In a second such image, the focus may be reset to image a different plane that lies a certain distance above (i.e. on the sample side) the platen, and so on. In some embodiments, the imaging system for such a variable focus imager is configured to be telecentric, providing a series of overlapping images even in portions that are out of focus.

Embodiments may alternatively or additionally use an imaging system with a fixed focus but a relatively large depth of focus, i.e. in lieu of or in addition to using an imaging system with variable focus. In such cases, the imaging system may thus be set such that the region of adequate focus includes the surface of the platen and some distance above it (i.e. on the sample side) to adequately image a larger portion of the sample. In some cases, such an imager provides telecentric imaging, which ensures that out-of-focus regions are spatially registered with other, in-focus planes.

Merely by way of illustration, in instances where the skin site comprises a finger, embodiments that provide for different focal planes permit features other than fingerprint features to be extracted from some or all of the image planes. For example, such features as deep blood vessels may be detected using one or more of the image planes with wavelengths that are highly absorbed by blood, which may include oxygenated hemoglobin peaks at approximately 540 nm and 576 nm. In some cases, multiple image planes corresponding to multiple illumination wavelengths are analyzed to identify features that have a spectral signature corresponding to blood or other skin constituents.

Methods of the invention are summarized with the flow diagram of FIG. 1. While FIG. 1 sets forth a number of steps that may be performed in particular embodiments, the invention encompasses other embodiments as well. In particular, the order of the steps shown is not intended to be limiting, and the inclusion of specific steps in the flow diagram is not intended to be limiting—some of the steps may be omitted in some alternative embodiments and some additional steps not illustrated explicitly may additionally be performed in some alternative embodiments.

The method begins at block 104 with a user placing a skin site on the platen of a biometric sensor. While the description that follows makes reference to a "skin site," it should be recognized that embodiments of the invention are more generally applicable to sensing and analysis of any purported skin site since the multispectral techniques described herein have the ability to discriminate between actual living tissue and a variety of spoofs. Multispectral measurements are performed on the skin site, with the measurement sequence being triggered manually or automatically in different embodiments. Automatic triggering may be accomplished with a mechanism that includes optical switches, capacitive switches, pressure switches, mechanical switches, and the like, and may advantageously make use of one or more cameras suitably positioned and having image processing to detect placement of the skin site in real time.

The measurement sequence may begin at block 108 by illuminating the skin site under the multispectral conditions. Such illumination is generally performed during a single illumination session for a substantially fixed position of the skin site. It will be appreciated by those of skill in the art that even in a single illumination session, illumination under the multispectral conditions may be achieved substantially simultaneously or may be achieved sequentially. Whether the illumination is substantially simultaneous or sequential may depend in part on the specific character of the multispectral conditions, and different examples of specific structures below illustrate configurations where substantially simultaneous illumination may be achieved for certain types of multispectral conditions. When the illumination is performed sequentially, the sequence spans a period of time sufficiently small, usually less than one second, that movement of the skin site during the sequence is minimal.

Light is accordingly received from the skin site at block 112. The received light may include light reflected at a surface of the skin site, such as from the platen-skin interface, and/or may include light scattered from beneath the surface of the skin site. Such subsurface scattering provides information not available in traditional fingerprint-imaging techniques. In particular, the ability to extract subsurface biometric information provides a mechanism for performing biometric determinations even in those cases where the surface features are missing or damaged. In this way, embodiments of the invention are advantageously robust to non-ideal skin qualities such as dryness, excessive wetness, lack of resilience, and/or worn features such as are typically associated with the elderly, those who perform significant manual labor, or those whose skin is exposed to chemicals, such as hairdressers or nurses.

Images are generated from the received light at block 116 by some manner of processing. Processing may include the extraction of different images from a single composite image. Processing may also include image-processing steps such as histogram equalization, contrast enhancement, edge enhancements, noise filtering, and the like. Image segmentation may be performed to mask out the image background and leave just the region in which the sample is present. As indicated at block 120, processing may also include performing transformations on one or more of the images to spatially register an image with other images. Identification of the spatial relationship among the images permits the presence of identified biometric features among multiple images to be correlated.

The processing of the images to extract such biometric features is performed at block 124. For example, in embodiments where the skin site comprises a finger, minutia points may be found on each of the individual images. Similarly, the overall pattern of ridges and valleys may be determined, or specific regions of interest such as core regions of the fingerprint may be identified on the images. In some cases, certain images or a combination of images may be analyzed to determine blood features or other spectrally distinct characteristics present in the image. The biometric features may comprise a set of coefficients formed by the decomposition of fingerprint features in a local area on to an appropriate set of basis functions such as sinusoids, Gabor filters, or various wavelets. Such identification of biometric features may advantageously avoid the adverse affects conventionally resulting from artifacts present in an image. This identification thus differs from identifications in conventional fingerprint images in which various factors such as skin dryness may result in the image being of extremely low contrast so that ridges appear to be noncontinuous, making it difficult to distinguish minutia points from simple image artifacts.

In embodiments in which biometric features are found on a plurality of image planes, those features may be combined as indicated at block 128. Since the images are spatially related to each other and represent the same skin-site placement, the locations of the features are well defined between images. Features may accordingly be assessed and combined individually by appropriate mathematical operations such as averaging, by such logical combination operations as "and" or "or," or by voting on the presence of a particular feature across image planes. The combined feature set may contain some indication of which image planes the individual feature originated from, or some other designator of the feature type or origin.

For example, a composite feature might be generated in one embodiment by a rule that declares a composite feature to be present at a defined location if the feature (e.g., a minutia point) is present in at least one of the image planes at that location. In another embodiment, a composite feature may be declared to be present at a location if the feature is present in at least half (or some other specified fraction) of the image planes at that location. Another embodiment might require that the feature be present in all the image planes at that location to be able to declare the presence of a composite feature. In a further embodiment, a composite feature might be generated by a rule that declares a composite feature to be present at a defined location only if the feature is present in all of the image planes that have identifiable characteristics in the vicinity of the feature location. Still other rules that may be applied in different embodiments to declare the presence of a composite feature will be evident to those of skill in the art after reading this description.

The information from the images may be combined at different stages in the process, notably prior to the feature-extraction stage of block 124 in some embodiments. For example, raw images may be combined in some manner, such as through pixel-by-pixel summation, or preprocessed images may be combined in some manner. In other instances, values derived from the images, such as Gabor wavelet coefficients or gradient fields, may be combined through such calculations as determining an average, a robust mean, a median, etc.

Furthermore, in some embodiments features may be identified by examining a combination of images. Merely by way of example, in one embodiment, blood features may be found by estimating the amount of blood present at each pixel location in each of a set of images that correspond to a plurality of illumination wavelengths based on the known absorbance spectrum of blood. Mathematical procedures such as classical least-squares estimation and a variety of other known estimation methods may be used to perform such analyses.

The set of features may the be processed under typical biometric operations to perform a biometric function such as enrollment, verification, identification, and/or spoof detection. For instance, the individual who supplied the skin site may be identified or his identity may be verified. Such biometric functions may be performed in some embodiments as indicated at block 132 by comparing the derived combinations of biometric features with a database of features. For instance, a database may include a specification of combinations of biometric features obtained from many individuals as part of an enrollment process, with the biometric function being performed at block 132 through a comparison of the combination generated at block 128 with entries in the database.

Figure 2:
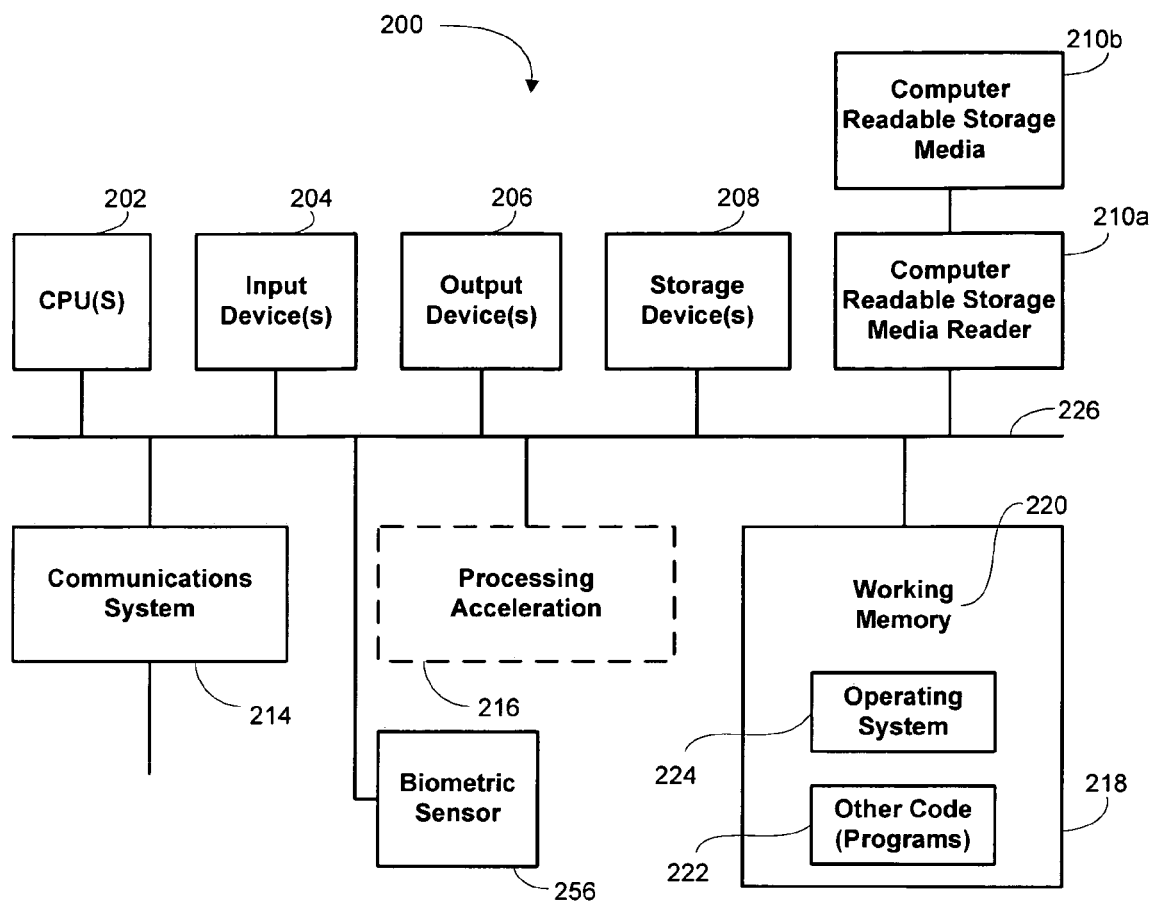
FIG. 2 is a schematic diagram showing the functional structure of a biometric system in accordance with embodiments of the invention.

A general overview of the structure of biometric system suitable for implementing the method(s) of FIG. 1 is provided with the schematic diagram of FIG. 2. FIG. 2 broadly illustrates how individual system elements may be implemented in a separated or more integrated manner. The biometric system 200 is shown comprised of hardware elements that are electrically coupled via bus 226. The hardware elements include a processor 202, an input device 204, an output device 206, a storage device 208, a computer-readable storage media reader 210a, a communications system 214, a processing acceleration unit 216 such as a DSP or special-purpose processor, and a memory 218. The computer-readable storage media reader 210a is further connected to a computer-readable storage medium 210b, the combination comprehensively representing remote, local, fixed, and/or removable storage devices plus storage media for temporarily and/or more permanently containing computer-readable information. The communications system 214 may comprise a wired, wireless, modem, and/or other type of interfacing connection and permits data to be exchanged with external devices. The multispectral data are collected by a biometric sensor 256, which may also be coupled electrically via bus 226.

Figure 3A:
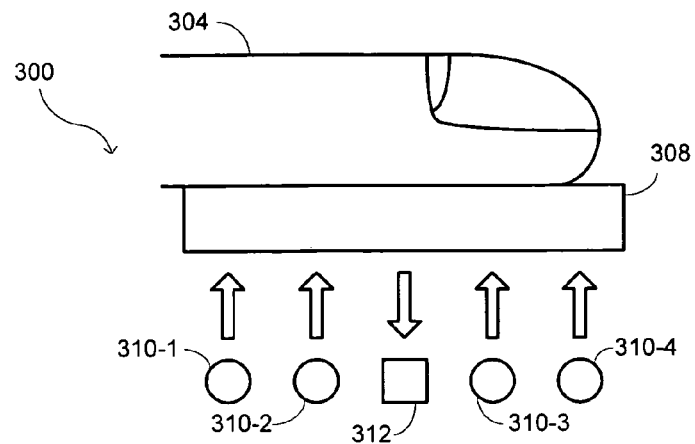
FIGS. 3A-3C provide illustrations of biometric sensors that permit collection of multispectral data according to different embodiments of the invention that provide different illumination wavelengths and/or different polarization conditions.

The biometric system 200 also comprises software elements, shown as being currently located within working memory 220, including an operating system 224 and other code 222, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed A variety of different structures that may be used for the biometric sensor 256 in different embodiments are provided for illustrative purposes in FIGS. 3A-6. For example, FIG. 3A shows an example of a biometric sensor 300 that incorporates multiple illumination wavelengths in providing the multispectral conditions. The multiple wavelengths will generally interact differently with different components of a finger or other tissue presented by a user as part of a biometric function. For example, wavelengths less than approximately 600 nm are strongly absorbed by blood, with particularly strong peaks at approximately 540 nm and 576 nm due to oxygenated hemoglobin. Also, in general, longer wavelengths of light (e.g. red or infrared light) penetrate the skin more deeply and are affected by deeper structures; shorter wavelengths (e.g. blue or near-ultraviolet) penetrate less deeply and are strongly affected by surface and near-surface skin structures.

The skin site 304 in FIG. 3A rests on a platen 308, which may be transparent or translucent at the wavelengths used to illuminate the skin site 304. A light detector 312, such as a digital camera, is used to form an image of the skin of the skin site 304 near the interface with the platen 308 using various lenses, mirrors, and/or other optical elements (not shown in FIG. 3A). The detector 312 may be sensitive to a broad range of wavelengths. In some cases, the detector 312 might incorporate a silicon digital imaging chip. Such a silicon-based camera might be a "black and white" camera, capable of detecting a broad range of wavelength spanning approximately 350 nm to 1100 nm.

The sources of illumination 310 may be provided as quasi-monochromatic sources of different wavelengths. Examples of suitable sources 310 include light emitting diodes ("LEDs"), lasers, laser diodes, quantum dots, filtered incandescent sources, and the like. In an embodiment where the detector 312 comprises a silicon-based sensor, the wavelengths of the light sources 310 may be chosen to lie in the range of approximately 350 nm to 1100 nm. In one embodiment, the light sources lie in the visible region of approximately 400-700 nm. The light from each source 310 may be spread out and directed towards the skin site 304 using a variety of methods. For instance, the light may be expanded and collimated using such optical elements as lenses and/or mirrors. The light may be diffused using a scattering medium such as a piece of frosted glass material, opal glass, a holographic diffuser, translucent plastic, and other mechanisms known in the art.

The sequence of operation of the sensor 300 may be sequential illumination in which a first light source 310-1 of a particular wavelength is illuminated to permit the detector 312 to acquire and store an image. The first light source 310-1 is then extinguished and a second light source 310-2 is illuminated after which the detector 312 acquires and stores the next image. This sequence continues for all the light sources 310 and may be repeated some number of times. Alternatively, each light source 310 may be modulated at a certain unique frequency, with the detector 312 acquiring a series of images at a frequency that is generally different than any of the illumination modulation frequencies. The resulting images may then be analyzed to estimate the contributions of the individual illumination wavelengths using methods known in the art.

Figure 3B:
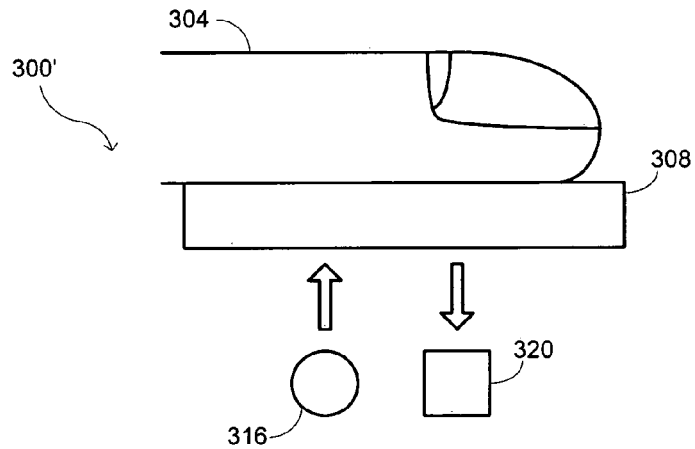

FIG. 3B illustrates a variant of the multiple-wavelength embodiment. In this case, the biometric sensor 300' comprises an illumination source 316 that is provided as a broadband source, such as an unfiltered incandescent lamp or a white-light LED. In addition to the functionality of the detector 312 in the embodiment of FIG. 3A, a detector 320 is equipped to perform an optical filtering operation. One method for doing so is to incorporate a color filter array (not shown) on the surface of the imaging array similar to a Bayer pattern commonly used on color cameras. Another method is to incorporate a color beam splitter that directs different color images to multiple detectors.

The sequence of operation for the system shown in FIG. 3B may thus be to collect one or more images after the broadband source 316 is illuminated. The individual color images may then be extracted as a set of subpixels in the case of a color filter array, or read out from individual detectors in the case of a color beam splitter.

Figure 3C:
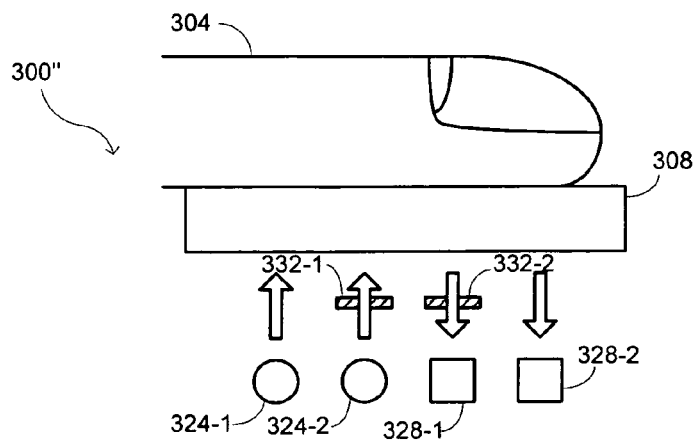

FIG. 3C depicts a biometric sensor 300" that incorporates different polarization conditions to collect multiple, different images of the skin site 304. Polarization of light is affected by optical scattering that occurs in the tissue or other scattering medium. For this reason, crossed linear polarizers may be implemented to discriminate against surface reflections and emphasize light that has interacted deeper in the tissue. In similar ways, parallel linear polarization and various elliptical polarization configurations may be employed to emphasize different features of the tissue. In a related way, polarization, and especially linear polarization, affects the magnitude of reflection that occurs at optical interfaces through Fresnel reflection phenomena. As such, different linear polarizing orientations may be employed to emphasize or de-emphasize light reflected from one or more interfaces.

In FIG. 3C, the skin site 304 is illuminated through the platen 308 by light sources 324 and is imaged by detectors 328 in a manner similar to that described in connection with FIGS. 3A and 3B. The light sources 324 may be quasimonochromatic or broadband and the detectors 328 may be black-and-white or color in the manner described in connection with those drawings. The light from some (or all) of the illumination sources 324 may be polarized by a polarizing element 332-1. The polarizer 332-1 may comprise a linear polarizer or an elliptical polarizer in different embodiments. Similarly, some of the detectors 328 may view the image through a second polarizer 332-2, which may also be a linear or elliptical polarizer in different embodiments.

In one embodiment, the illumination polarizer 332-1 and detection polarizer 332-2 are linear polarizers arranged such that the optical axes of the two polarizers 332 are substantially orthogonal. In other cases, the polarizers 332 are arranged to have substantially parallel polarizations.

In the case where either polarizer 332 comprises an elliptical polarizer, the elliptical polarizer may be preceded by a linear polarizer (not shown in FIG. 3C) oriented at some angle relative to the axis of the elliptical polarizer. This angle may be chosen to produce right-circular or left-circular light in a manner known to one familiar in the art. In one embodiment, elliptical polarizers comprised by polarizers 332 are arranged such that both polarizers 332 produce left-circular light or both polarizers 332 produce right-circular light. In another embodiment, one polarizer 332 may produce left-circular light while the other polarizer 332 produces right-circular light.

As illustrated in FIG. 3C, nonpolarized sources 324 may also be present, producing illumination conditions that are viewed by a polarized detector 328-1. Embodiments may also have an unpolarized camera 328-2 that views an image produced using light from a polarized source 324-2.

Figure 4:
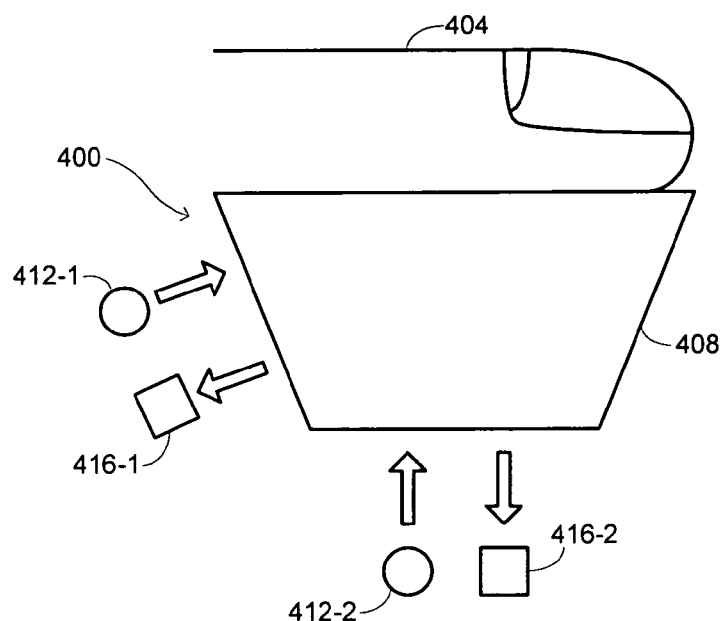
FIG. 4 provides an illustration of a biometric sensor that permits collection of multispectral data in another embodiment of the invention that provides multiple illumination and detection angles.

The use of multiple angles of illumination and imaging is illustrated with the biometric sensor shown in FIG. 4. A change in the angle of illumination or detection generally causes a change in the magnitude and/or direction of light transmitted or reflected from an optical interface. At a certain angle known as the critical angle, the interface between media of two different indices of refraction can produce total internal reflectance effects. Observing a skin site in contact with a platen on either side of the platen-air critical angle can produce markedly different images with distinctly different information content. There are also possible shadow-casting effects that occur for irregular features such as the external fingerprint patterns, as well as a variety of polarization effects. All of these kinds of effects alter the nature of the images that are produced by imagers under different optical angles of illumination and detection.

FIG. 4 shows a plurality of illumination sources 412 illumination a skin site 404 through a prism 408 that acts as or comprises the platen. There are also a plurality of detectors 416 viewing the skin site 404 through the prism 408. The use of a prism minimizes optical effects that occur at the interface where light enters or leaves the platen material. Other forms of platen may alternatively be employed, including microprism arrays and simple planar windows. In the drawing, light from the illumination sources 412 may be quasicollimated prior to illuminating the skin site 404. Any or all of the detectors 416 may collect image data when the skin site 404 is illuminated by any or all of the illumination sources 412. In some cases, one or more of the light sources, such as source 412-1 in the drawing, may be oriented at an angle greater than the critical angle defined by the platen-air interface, causing total internal reflection effects at the interface between the skin site 404 and platen. In some cases, one or more of the detectors, such as detector 416-1 in the drawing, may similarly be oriented at an angle greater than the critical angle defined by the platen-air interface, causing the images produced by the detector to be affected by total internal reflectance effects.

Figure 5A:
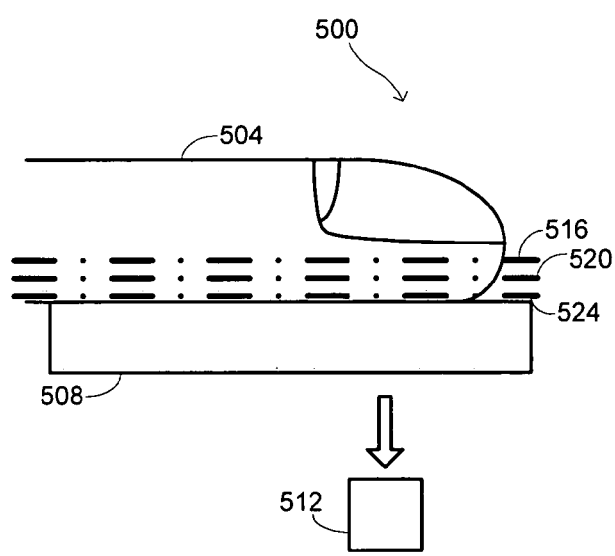
FIGS. 5A and 5B respectively provide side and front views of a biometric sensor that permits collection of multispectral data in a further embodiment that provides multiple focal planes.
Figure 5B:
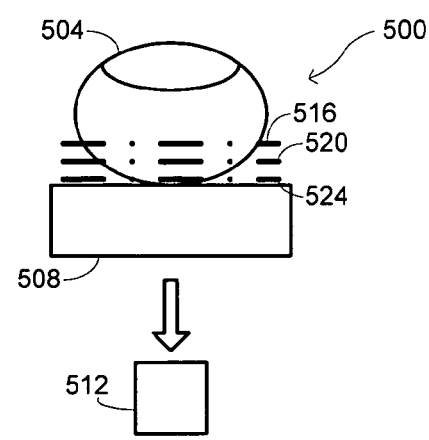

FIGS. 5A and 5B show a portion of a biometric sensor 500 that can collect images with multiple focal planes. FIG. 5A illustrates a side view of such a biometric sensor 500 while FIG. 5B shows a front view of the sensor 500. The skin site 504 rests on a platen 508. The side view of FIG. 5B illustrates the tendency when the skin site 504 is comprised by a curved body portion, such as by a finger, to have regions that are not in contact with the platen 508. A detector 512 with a variable focus thus permits a collection of images to be captured that have different focal planes. For example, a first such image may be acquired by the detector 512 with the focus set such that the image is optimum along plane 524, substantially at the interface between the skin site 504 and the platen 508. The next such image may be acquired with the focus of the detector 508 reset to image a plane 520 that lies above the platen 508. A third such image may be acquired when the detector 512 has the focus set to image still another plane 516, and so on.

An imaging system comprised by the detector 512 may comprise lenses, mirrors, and other optical elements (not shown in FIGS. 5A or 5B) to achieved the desired focus, with the mechanism for varying the focus with such optical elements comprising electromechanical assemblies, liquid lens elements that use electrostatic forces acting on fluid-filled elements, deformable mirrors, MEMS-based components, and the like. In some embodiments, the imaging system comprised by the detector 512 may be configured to provide telecentric imaging, thereby maintaining registration of features in the images collected under different focal settings.

In some embodiments, a fixed-focus imaging system may be used with the detector 512 where the imaging system is designed to provide a sufficient depth of focus. For example, a fixed-focus system may be used-in which focal planes 516, 520, and 524 are all focused with sufficient resolution and image quality. Typically fingerprint features are imaged by systems that have resolutions of approximately 500 pixels per inch (ppi), but this requirement can vary widely from about 100 ppi to about 4000 ppi, depending on the application requirements. Imaging-system designs that maintain the ability to image features over a specified focus region with the required resolution are known to those of skill in the art. In some cases, such an imaging system is also designed to provide telecentric imaging characteristics.

Figure 6:
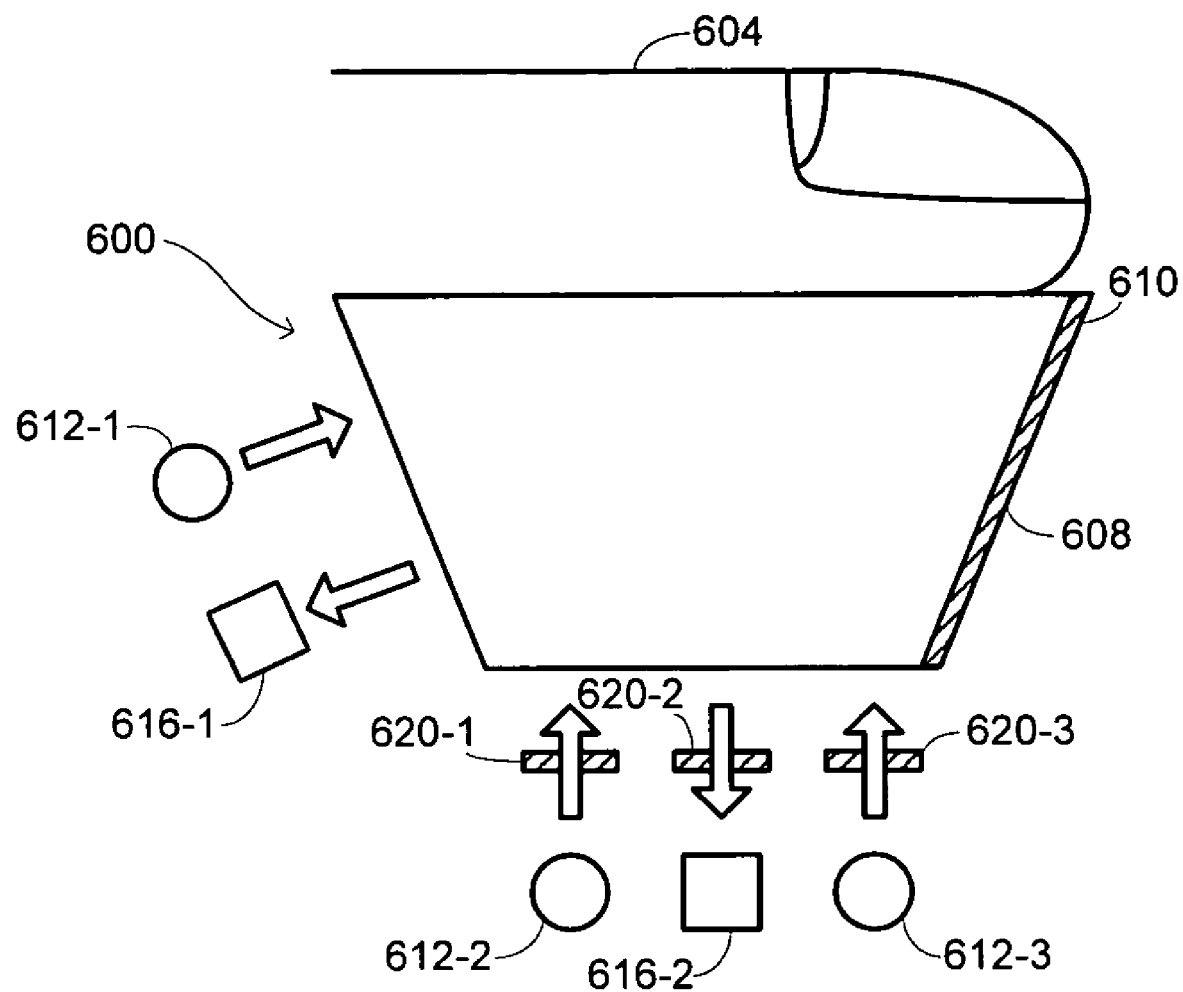
FIG. 6 provides an illustration of a biometric sensor that combines aspects of the biometric sensors of FIGS. 3A-5B to permit collection of multispectral data with multiple illumination wavelengths, multiple polarization conditions, multiple illumination angles, multiple detection angles, and multiple image planes.

FIG. 6 shows an embodiment of the invention that combines several different mechanisms for collecting multispectral data by combining the different mechanisms to produce multiple images under different optical conditions. The skin site 604 is provided in contact with a platen 608 made from a prism. The right-side facet of the prism 608 in the drawing is coated with a diffuse optical reflective coating 610. Light from sources 612-2 and 612-3 respectively pass through polarizer 620-1 and 620-3 before entering the prism and illuminating the skin site 604. Light from source 612-1 passes into the prism without first passing through a polarizer. The wavelengths of light emitted by the various sources 612 may be substantially different from each other. The polarizers 620-1 and 620-. may be linear polarizers of substantially the same orientation in a particular embodiment.

The detector 616-2 views the skin site 604 through a polarizer 620-2 and the prism 608. This polarizer 620-2 may be a linear polarizer oriented to be substantially orthogonal to the illumination polarizers 620-1 and 620-3. The detector 616-1 views the skin site 604 through the prism 608 without an intervening polarizer. This detector 616-1 may be oriented such that it is substantially affected by TIR at the interface between the skin site 604 and the prism 608.

Imaging systems comprised by either or both of detectors 616 may provide for taking images with varying focal planes. In one embodiment, detector 616-2 may be adapted to collect multiple images with different focus settings to adequately image portions of the skin site 604 not in contact with the platen 608. Alternatively, the imaging system for detector 616-2 may be a fixed-focus system with a depth of focus chosen such that a desired amount of the skin site 604 that is not in contact with the platen 608 is imaged with adequate resolution. In the case of either variable focus or fixed focus, the imaging system may be further adapted to provide telecentric imaging capability.

Light from source 612-1 passes into the prism 608 and is diffusely reflected by the coating 610 to illuminate the interface between the skin site 604 and the platen 610. The skin site is imaged by the plurality detectors 616. After the images are acquired under illumination from source 612-1, this source is turned off and source 612-2 is turned on. Either or both detectors 616 may take a second set of images. This sequence is then repeated for source 612-3.

It will be appreciated that while FIG. 6 shows a specific number of sources and detectors, and a specific number of those sources and detectors providing or receiving light that is polarized, this is for illustrative purposes only. More generally, embodiments may combine any of the various aspects for generating multispectral data described above. For instance, the embodiment of FIG. 6 might be modified so that only unpolarized light is used or so that only a single focus plane is used. Furthermore, alternative embodiments may more generally use any number of sources and detectors, and may have any number of such sources and detectors disposed to provide light through a polarizer or receive light through a polarizer.

Figure 7:
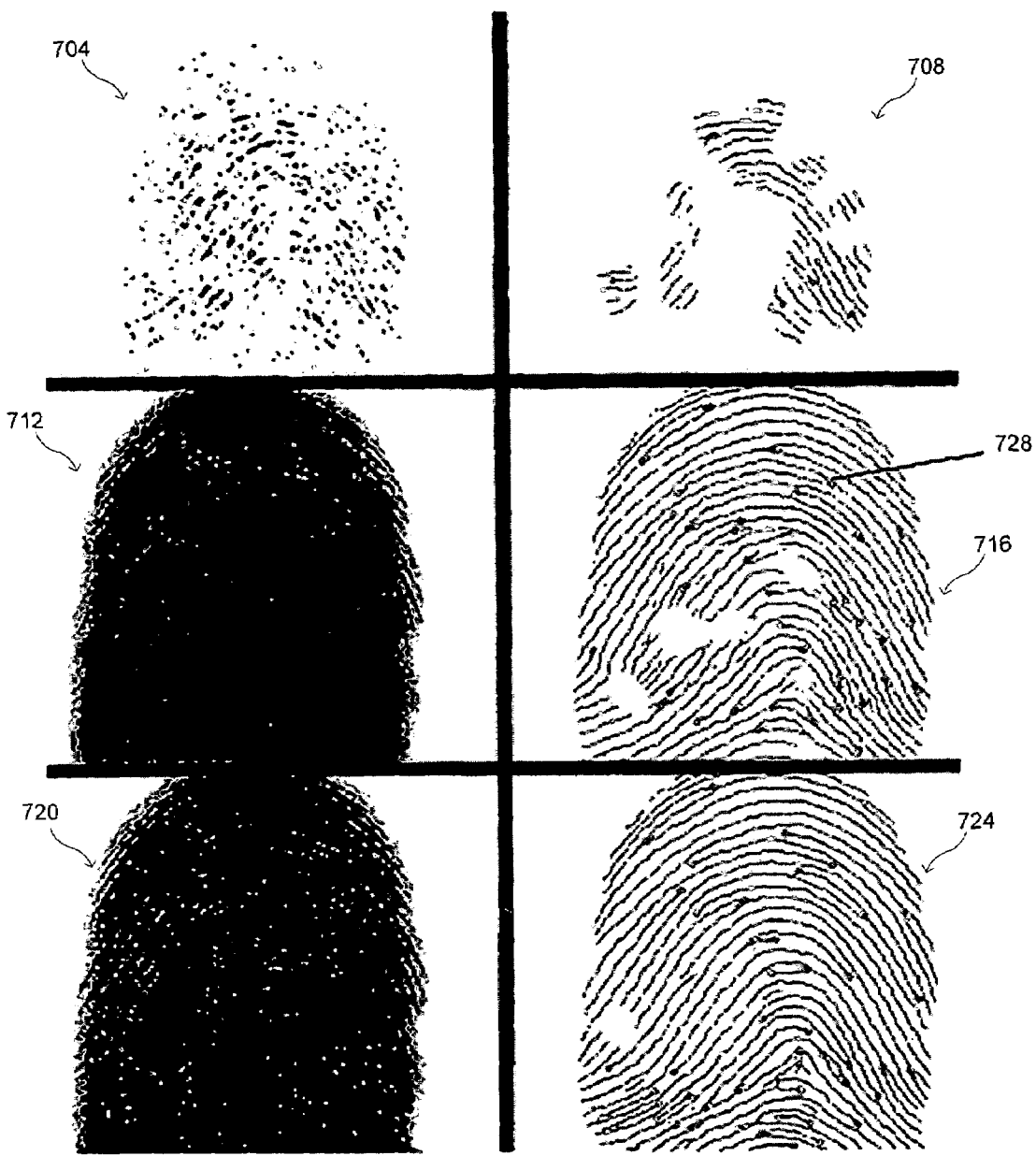
FIG. 7 shows raw and processed images from three different optical configurations used to image a finger having dry skin during a single placement on a platen of a biometric sensor of the invention.

FIG. 7 shows some data generated by a system constructed in accordance with the configuration of FIG. 6. The skin site that was imaged was a finger that was particularly dry after being exposed for ten minutes to a clay-based desiccant prior to imaging. The images on the left side of the drawing, identified by reference numbers 704, 712, and 720, are the images that result from various optical conditions viewing the dry finger after initial preprocessing. They thus correspond to images produced at block 116 of FIG. 1.

The images on the right side of FIG. 7, identified by reference numbers 708, 716, and 724, are the result of performing the biometric feature extraction described above on the respective left-side images, i.e. image 708 is the result of performing the biometric feature extraction on image 704, image 716 is the result of performing the biometric feature extraction on image 712, and image 724 is the result of performing the biometric feature extraction on image 720. Each of the right-side images 708, 716, and 724 shows a skeletonized version of the image to its left, as well as any minutia points that were found, an example of which is denoted by reference number 728. The skeletonized images with minutia points 708, 716, and 724 correspond to images produced at block 128 of FIG. 1

Briefly, skeletonization of images is a process for reducing foreground regions in an image to a skeletal remnant. This remnant largely preserves the extent and connectivity of the original region, while discarding most of the original foreground pixels. Skeletonization is typically performed in one of two ways. With one class of techniques, a morphological thinning is provided that successively erodes away pixels from the edges of each ridge line in such a way that no more thinning is possible and the medial line is left. What remains approximates the skeleton. With the other class of techniques, a distance transform of the image is calculated, with the skeleton lying along the singularities in the distance transform. In either case, the resulting skeletonized image may be processed to define points at which the lines end or bifurcate using methods known in the art. These points are known as minutia points and their use in biometric tasks is well known. Alternatively, methods may be applied directly to the original grayscale (nonskeletonized) images to extract a similar set of minutia points using techniques known in the art.

Image 704 was collected using an optical arrangement that corresponds to using illumination source 612-1 and detector 616-1 in FIG. 6. This is a typical TIR-based measurement configuration. As is evident in FIG. 7, the TIR image is badly degraded due to the dry quality of the finger being observed. This deterioration results in a small number of minutia points being identified in image 708, which in turn leads to relatively poor biometric- system performance.

Image 712 was collected using an optical arrangement that corresponds to using illumination source 612-2 and detector 616-2 in FIG. 6. Linear polarizers corresponding to polarizers 620-1 and 620-2 were arranged in a substantially orthogonal orientation. Image 720 was collected using an optical arrangement that corresponds to using illumination source 612-1 and detector 616-2 in FIG. 6, viewing the finger through polarizer 620-2. In this case, the wavelengths of the sources 612-1 and 612-2 were similar, being red light with a wavelength of approximately 635 nm. The resulting images 712 and 720 produced more and better biometric features in the corresponding skeletonized images 716 and 724, as illustrated by a comparison of those images with image 708.

Figure 8:
FIG. 8 shows raw and processed images from three different optical configurations used to image a finger making minimal contact with a platen of a biometric sensor of the invention.

FIG. 8 shows a similar set of data produced by the same system, but in this case were derived from data collected when the person's finger touched the sensor very lightly, causing a very small region of contact. The layout of images is the same as that in FIG. 7. That is, images 804, 812, and 820 correspond to preprocessed images respectively collected under TIR conditions, with a crossed polarization configuration, and with various illumination/detection angles, and images 808, 816, and 824 are corresponding results after feature extraction. Because of the small region of contact, the TIR image 804 produced by illumination with source 612-1 and imaging by detector 616-1 has a greatly reduced area over which fingerprint features can be seen. The corresponding processed image 808 also shows the greatly reduced number of features that can be extracted from this image.

This is in marked contrast to images 812 and 820, both of which were collected using detector 616-2, which has a relatively large focal distance. These images show the full fingerprint area notwithstanding the smallness of the region of contact. The corresponding feature-extraction images 816 and 824 demonstrate the ability of the methods and systems described above to extract biometric features in regions beyond the area of contact between the skin site and the sensor.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method of performing a biometric function, the method comprising:
   illuminating a purported skin site of an individual under a plurality of distinct optical conditions for a substantially fixed position of the purported skin site;
   focusing an imager at a first focal plane of the purported skin site;
   receiving light at the imager from the first focal plane of the purported skin site;
   focusing the imager at a second focal plane of the purported skin site;
   receiving light at the imager from the second focal plane of the purported skin site;
   generating a plurality of multispectral images of the purported skin site from the light received from the first focal plane and the second focal plane; and
   identifying a biometric feature using the plurality of multispectral images.

2. The method recited in claim 1 wherein the biometric feature is a characteristic common to respective portions of multiple of the plurality of images.

3. The method recited in claim 1 wherein the biometric feature comprises a plurality of biometric features.

4. The method recited in claim 3 wherein the identifying a biometric feature comprises:
   identifying a spatial relationship among the plurality of multispectral images from a condition that placement of the purported skin site is common for each of the plurality of multispectral images; and
   identifying the plurality of biometric features from the identified spatial relationship.

5. The method recited in claim 3 further comprising comparing the plurality of biometric features with a set of biometric features stored in a database relating sets of biometric features with identified individuals.

6. The method recited in claim 1 wherein:
   the purported skin site comprises a finger of the individual;
   the plurality of multispectral images comprise a plurality of multispectral fingerprint images; and
   the biometric feature comprises a minutia point of at least one of the plurality of multispectral fingerprint images.

7. The method recited in claim 1 wherein the illuminating illuminates the purported skin site under a plurality of distinct illumination wavelengths.

8. The method recited in claim 1 wherein the illuminating illuminates the purported skin site under a plurality of distinct polarization conditions.

9. The method recited in claim 1 wherein the illuminating illuminates the purported skin site under a plurality of distinct illumination orientations for illuminating the purported skin site during the illumination session.

10. The method recited in claim 1 further comprising receiving light from a third focal plane of the purported skin site during the illumination session; and generating a plurality of multispectral images of the purported skin site from the light received from the first focal plane, the second focal plane, and the third focal plane.

11. The method recited in claim 1 further comprising identifying the individual or verifying an identity of the individual.

12. The method recited in claim 1 wherein receiving light from the second focal plane of the purported skin site comprises receiving light scattered from beneath a surface of the purported skin site.

13. The method recited in claim 1 wherein the plurality of multispectral images comprises a total-internal-reflectance ("TIR") image of the skin site and a non-TIR image of the skin site.

14. The method recited in claim 1 wherein:
   the purported skin site comprises a finger of the individual;
   the purported skin site is in contact with a platen;
   the plurality of images comprises a multispectral fingerprint image; and
   the biometric feature comprises a biometric feature of the individual identified outside an area of contact of the purported skin site with the platen.

15. The method recited in claim 1 wherein analyzing the plurality of multispectral images comprises:
   skeletonizing the at least one of the multispectral images; and
   identifying the biometric feature in the skeletonized at least one of the multispectral images.

16. The method recited in claim 1 wherein:
analyzing the plurality of multispectral images comprises performing a decomposition of the portion of the at least one of the images onto a set of basis functions; and
the biometric feature comprises a set of coefficients formed by the decomposition.

17. The method recited in claim 1 wherein the biometric feature comprises a representation of ridges and valleys on the skin site.

18. The method recited in claim 1 wherein the biometric feature comprises a characteristic of a presence of blood vessels beneath a surface of the purported skin site.

19. A biometric system comprising:
a platen adapted for placement of a purported skin site by an individual;
an illumination source disposed to illuminate the purported skin site under a plurality of distinct optical conditions when placed on the platen;
an imaging system configured to focus at a first focal plane of the purported skin site during a first focusing event, and configured to focus at a second focal plane of the purported skin site during a second focusing event; and
a controller interfaced with the illumination source and the imaging system, the controller including:
instructions to illuminate the purported skin site with the illumination source during an illumination session for a substantially fixed position of the purported skin site;
instructions to focus the imaging system at a first focal plane of the purported skin site;
instructions to capture light at the imaging system from the first focal plane of the purported skin site separately for each of the plurality of distinct optical conditions;
instructions to focus the imaging system at a second focal plane of the purported skin site;
instructions to capture light at the imaging system from the second focal plane of the purported skin site separately for each of the plurality of distinct optical conditions from the second focal plane of the purported skin site;
instructions to generate a plurality of multispectral images of the purported skin site from the light received by the imaging system from at least the first focal plane and the second focal plane of the purported skin site; and
instructions to identify a biometric feature using the plurality of multispectral images.

20. The biometric system recited in claim 19 wherein the biometric feature is a characteristic common to respective portions of multiple of the plurality of multispectral images.

21. The biometric system recited in claim 19 wherein the biometric feature comprises a plurality of biometric features.

22. The biometric system recited in claim 21 further comprising:
instructions to identify a spatial relationship among the plurality of multispectral images from a condition that placement of the purported skin site on the platen is common for each of the plurality of multispectral images; and
instructions to identify the plurality of biometric features from the identified spatial relationship.

23. The biometric system recited in claim 21 further comprising a database interfaced with the controller, the database relating sets of biometric features with identified individuals, wherein the instructions to implement the biometric function comprise instructions to compare the plurality of biometric features with a set of biometric features stored in the database.

24. The biometric system recited in claim 19 further comprising a first polarizer disposed to polarize light provided by the illumination source, wherein:
the imaging system comprises a second polarizer disposed to polarize the light received from the purported skin site; and
the plurality of distinct optical conditions comprise distinct relative polarization conditions.

25. The biometric system recited in claim 19 further comprising a first polarizer disposed to polarize light provided by the illumination source, wherein:
the imaging system comprises a second polarizer disposed to polarize the light received from the purported skin site; and
the first and second polarizers are substantially in a crossed configuration.

26. The biometric system recited in claim 19 wherein:
the imaging system comprises a color filter array having a plurality of distributed filter elements, each filter element being adapted to transmit light of one of a limited number of specified narrowband wavelength ranges; and
the plurality of distinct optical conditions comprise distinct wavelengths of illumination light within the specified narrowband wavelength ranges.

27. The biometric system recited in claim 26 wherein the instructions to illuminate the purported skin site comprises instructions to illuminate the purported skin site with different wavelength sequentially.

28. The biometric system recited in claim 19 wherein the controller further includes instructions to illuminate the purported skin site with light from within the platen at an angle greater than a critical angle defined by an interface of the platen with an environment external to the platen, wherein the instructions to generate a plurality of images of the purported skin sited from light received by the imaging system comprise instructions to generate at least one of the plurality of images as an image of surface structure of the purported skin site from light incident on the interface of the platen where the purported skin site is in contact with the platen.

29. The biometric system recited in claim 19 wherein the instructions to analyze the plurality of multispectral images comprise:
instructions to skeletonize the at least one of the multispectral images; and
instructions to identify the biometric feature in the skeletonized at least one of the multispectral images.

30. The biometric system recited in claim 19 wherein:
the instructions to analyze the plurality of images comprise instructions to perform a decomposition of the portion of the at least one of the multispectral images onto a set of basis functions; and
the biometric feature comprises a set of coefficients formed by the decomposition.

* * * * *